(12) United States Patent
Wu et al.

(10) Patent No.: US 10,309,928 B2
(45) Date of Patent: Jun. 4, 2019

(54) APPARATUS AND METHOD FOR ION MOBILITY SPECTROMETRY AND SAMPLE INTRODUCTION

(71) Applicants: Ching Wu, Boxborough, MA (US); Mark A. Osgood, Brookline, NH (US); Eugenie Hainsworth, Somerville, MA (US); Clinton Alawn Krueger, Milton, MA (US); Taeman Kim, Westford, MA (US)

(72) Inventors: Ching Wu, Boxborough, MA (US); Mark A. Osgood, Brookline, NH (US); Eugenie Hainsworth, Somerville, MA (US); Clinton Alawn Krueger, Milton, MA (US); Taeman Kim, Westford, MA (US)

(73) Assignee: Excellims Corporation, Acton, MA (US)

( * ) Notice: Subject to any disclaimer, the term of this patent is extended or adjusted under 35 U.S.C. 154(b) by 0 days.

(21) Appl. No.: 15/713,684

(22) Filed: Sep. 24, 2017

(65) Prior Publication Data

US 2018/0067078 A1 Mar. 8, 2018

Related U.S. Application Data

(63) Continuation of application No. 13/419,425, filed on Mar. 13, 2012.

(Continued)

(51) Int. Cl.
*H01J 49/00* (2006.01)
*H01J 49/04* (2006.01)
(Continued)

(52) U.S. Cl.
CPC ......... *G01N 27/622* (2013.01); *G01N 27/624* (2013.01); *H01J 49/067* (2013.01); *H01J 49/165* (2013.01)

(58) Field of Classification Search
None
See application file for complete search history.

(56) References Cited

U.S. PATENT DOCUMENTS 5,747,799 A * 5/1998 Franzen ............... H01J 49/0422
250/282
5,917,185 A * 6/1999 Yeung ................. H01J 49/0404
250/288

(Continued)

OTHER PUBLICATIONS

Wittmer et al., "Electrospray Ionization Ion Mobility Spectrometry", Anal. Chem. 1994.*

(Continued)

*Primary Examiner* — Michael J Logie (57) ABSTRACT

The IMS apparatus and methods described in this invention involve setting the ion detector at the highest potential of the drift tube and setting the ionization source at ground or near ground potential. The methods allow significantly simple sample introduction without the limitation of the high potential (voltage) concern of the front end sample delivery. The invention also describes bringing samples directly into the ion mobility drift tube. The invention further describes using single syringe for sample introduction via an electrospray ionization method.

18 Claims, 4 Drawing Sheets

Related U.S. Application Data (60) Provisional application No. 61/452,117, filed on Mar. 13, 2011.

(51) Int. Cl.
  *G01N 27/62* (2006.01)
  *H01J 49/16* (2006.01)
  *H01J 49/06* (2006.01)

(56) References Cited

U.S. PATENT DOCUMENTS

| | | | | |
|---|---|---|---|---|
| 6,458,597 | B1* | 10/2002 | Andrien, Jr. | H01J 49/0445 250/281 |
| 2005/0035287 | A1* | 2/2005 | Jolliffe | H01J 49/0468 250/288 |
| 2005/0109931 | A1* | 5/2005 | Schultz | H01J 49/0045 250/287 |
| 2011/0104027 | A1* | 5/2011 | Pawliszyn | A61B 10/0045 422/527 |
| 2011/0174966 | A1* | 7/2011 | Wollnik | H01J 49/0422 250/286 |
| 2012/0267548 | A1* | 10/2012 | Vidal-De-Miguel | H01J 49/0422 250/424 |
| 2013/0264493 | A1* | 10/2013 | Covey | H01J 49/02 250/429 |

OTHER PUBLICATIONS

Tam et al., "Secondary Electrospray Ionization—Ion Mobility Spectrometry for Explosive Vapor Detection", Anal. Chem. 2004, 76, 2741-2747.*

Wu et al. "Electrospray Ionization High-Resolution Ion Mobility Spectrometry—Mass Spectrometry" Anal. Chem. (Year: 1998).*

* cited by examiner

APPARATUS AND METHOD FOR ION MOBILITY SPECTROMETRY AND SAMPLE INTRODUCTION

PROVISIONAL PATENT APPLICATION

The present application is a continuation of U.S. patent application Ser. No. 13/419,425, filed Mar. 13, 2012, which claims the benefit of and priority to corresponding U.S. Provisional Patent Application No. 61/452,117, filed Mar. 13, 2011; the entire contents of these applications is herein incorporated by reference.

BACKGROUND OF THE INVENTION

The needle in some commercial electrospray ionization (ESI) sources is operated at kilovolt potentials during electrospray operation. For such ESI sources, a longer dielectric liquid transfer line of several inches is typically configured between the ground potential injector valve and the ESI needle to allow a gradual drop in kilovolt potential through the sample solution. A high electric field gradient in the transfer tube is avoided to minimize sample heating, electrophoretic and electrolysis effects during Flow injection analysis (FIA). Liquid transfer lines can be reduced in length when an ESI source in configured with a grounded needle, however, even with grounded ESI needles, the dead volume due to the transfer lines cannot be entirely eliminated. For ion mobility spectrometer (IMS) applications where small amounts of sample are available for injection, sample dilution or losses due to injector valve, connector and transfer line dead volumes and surfaces may compromise the limit of detection.

SUMMARY OF THE INVENTION

The IMS apparatus and methods described in this invention involve setting the ion detector at the highest potential of the drift tube and setting the ionization source at ground or near ground potential. The methods allow significantly simple sample introduction without the limitation of the high potential (voltage) concern of the front end sample delivery. The invention also describes bringing samples directly into the ion mobility drift tube. The invention further describes using single syringe for sample introduction via an electrospray ionization method.

This invention reduces or eliminates cross contamination, solvent consumption, liquid dead volume, and waste by having the sampling and spray needle the same apparatus. The sampling and spray needle configured with an auto injector apparatus, continuous infusion syringe pump, or used in manual injection is introduced directly into the IMS. Such a sampling and spray needle eliminates the need for injector valves, transfer lines or additional fluid delivery systems into IMS instruments. The injector needle and an ESI source has been configured such that the sample solution can be sprayed directly from the injector needle tip. The injector needle does not need to be introduced into the ESI source region through a guide. The needle can be configured as a reusable or disposable tip. The liquid spray flow rate is set by the auto or manual injector sample injection flow rate. This flow rate can be set to optimize IMS analysis and sample throughput. In addition, automation of the direct spray needle can be achieved by setting up array of the spray needles that are loaded in a manner that rotates and/or moves to the next spray needle in the ESI source region.

The invention comprises a reusable or disposable needle configured in an auto-injector or a manual injector which serves as the means to remove a sample solution from a container and transport such solution to an atmospheric pressure ionization (API) source (such as ESI or APCI) wherein the needle is to deliver sample directly into the API source and/or desolvation region. Such fixed or disposable needle, when introduced into an API source, becomes the liquid introduction channel or tube in the nebulizer probe of an APCI source, the nebulizer apparatus of a pneumatically assisted Electrospray probe or an Electrospray tip in an unassisted ESI ion source probe. Ions produced from samples introduced through such sprayers into an API source are subsequently directed into a desolvation region of the IMS. Auto injectors may be configured with multiple injector needles configured for direct delivery of sample into an API source through one or more probes. Such multiple needle auto injectors may deliver samples in a sequential or multiplexed manner to such single or multiple direct injection API source ports or probes to maximize sample throughput. In one embodiment of the invention, a reusable or disposable sampling and spray injection needle may be packed with material, such as C18 coated beads, to aid in desalting, sample cleanup or the separation of sample compounds in solution during the sample pickup, delivery and spray steps. Different solvent composition layers can be pulled sequentially into such packed sampling and spray needles with attached reservoirs prior to sample pickup. The sample can then be sprayed into an API source from such a loaded injection needle using solvent gradients to aid in sample desalting, additional cleanup or sample compound separation during spraying.

Washing or flushing of a packed or open disposable injection needle, according to the invention, is not required between injections allowing an increase in sample throughput. In one embodiment of the invention, sample solution may be drawn up into a packed or open disposable injection needle. The injection needle is subsequently introduced into the API source and sample solution is sprayed from the injection needle tip with or without a solvent gradient to elute sample from any packed material. Alternately, a sample solution can be loaded into a non-disposable or reusable needle and the needle is then inserted into and forms a seal with a packed disposable injection needle. The packed injection needle is then introduced into an API source and the sample solution and any solvent gradient flows from the non-disposable needle through the packed disposable needle. The resulting solvent and sample solution is sprayed from the disposable needle tip into an API source. The packing material in the disposable tip serves to desalt or further clean the sample solution as well as to provide some sample component separation due to solvent gradient flow, if desired. Depending on the requirements of a specific analytical application, packing material may be replaced by filter media according to the invention to aid in sample cleanup with a minimum of dead volume.

The invention eliminates the need for sample injector valves or transfer lines into an API source, reducing sample dilution, loss and contamination due to sample handing and transfer. When a reusable needle is configured in the invention, the needle inner bore and outer surface can be washed in between each sample delivery and spraying step to reduce or eliminate, chemical noise, cross talk or carry over from one sample to the next. The use of disposable needles, configured according to the invention, eliminates sample to sample cross talk or contamination without a wash step between sample injections into the API source. Faster cycle times or more rapid sample injection throughput can be achieved by eliminating wash steps. Alternatively, a wash step can be run for one or more reusable injection needles while sample delivery and spraying is occurring with another injection needle or needles. The invention reduces apparatus costs, sample losses, sample contamination, and sample handling and minimizes solvent consumption and waste while increasing sample throughput in flow injection analysis with Atmospheric pressure ion sources. A direct injection needle apparatus may be configured with other API inlets in the same API source chamber as a means to increase analytical flexibility within one API source apparatus. Ions produced from the API source may be analyzed by an apparatus other than MS including but not limited to ion mobility analyzers.

This invention also describes an apparatus and method for operating the ionization source and/or sample inlet at ground or near ground potential. The configuration will enable the direct electrospray and allow simple interface to API and other sample introduction methods, such as interface a thermal desorber, in this case the thermal desorption process can happen in the ionization region.

BRIEF DESCRIPTION OF THE DRAWINGS

The foregoing and other aspects, embodiments, and features of the inventions can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the inventions.

DETAILED DESCRIPTION OF VARIOUS EMBODIMENTS

Unless otherwise specified in this document the term "ion mobility based spectrometer" is intended to mean any device that separates ions based on their ion mobilities and/or mobility differences under the same or different physical and/or chemical conditions, the spectrometer may also include detecting the ions after the separation process. Many embodiments herein use the time of flight type IMS as examples; the term ion mobility based spectrometer shall also include many other kinds of spectrometers, such as differential mobility spectrometer (DMS) and field asymmetric ion mobility spectrometer (FAIMS). Unless otherwise specified, the term ion mobility spectrometer or IMS is used interchangeable with the term ion mobility based spectrometer defined above.

As used herein, the term "analytical instrument" generally refers to ion mobility based spectrometer, MS, and any other instruments that have the same or similar functions. Unless otherwise specified in this document the term "mass spectrometer" or MS is intended to mean any device or instrument that measures the mass to charge ratio of a chemical/biological compounds that have been converted to an ion or stores ions with the intention to determine the mass to charge ratio at a later time. Examples of MS include, but are not limited to: an ion trap mass spectrometer (ITMS), a time of flight mass spectrometer (TOFMS), and MS with one or more quadrupole mass filters The phrase "and/or," as used herein in the specification and in the claims, should be understood to mean "either or both" of the elements so conjoined, i.e., elements that are conjunctively present in some cases and disjunctively present in other cases.

The foregoing and other aspects, embodiments, and features of the inventions can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the inventions.

The term ion mobility separator, and ion mobility spectrometer, and ion mobility based spectrometers are used interchangeably in this invention, often referred to as IMS, including time-of-flight (TOF) IMS, differential mobility spectrometers (DMS), field asymmetric ion mobility spectrometers (FAIMS) and their derived forms. A time of flight ion mobility spectrometer and their derived forms refers to, in its broadest sense, any ion mobility based separation device that characterize ions based on their time of flight over a defined distance. A FAIMS, a DMS, and their derived forms separate ions based on their ion mobility characteristics under high values of normalized electric field. The IMS systems may operate in different drift media, such as gas and/or liquid, in their pure or mixture forms. The operating pressure may vary from low vacuum to a plurality of atmospheric pressures.

The systems and methods of the present inventions may make use of "drift tubes." The term "drift tube" is used herein in accordance with the accepted meaning of that term in the field of ion mobility spectrometry. A drift tube is a structure containing a neutral gas through which ions are moved under the influence of an electrical field. It is to be understood that a "drift tube" does not need to be in the form of a tube or cylinder. As understood in the art, a "drift tube" is not limited to the circular or elliptical cross-sections found in a cylinder, but can have any cross-sectional shape including, but not limited to, square, rectangular, circular, elliptical, semi-circular, triangular, etc. In many cases, a drift tube is also referred to the ion transportation and/or ion filter section of a FAIMS or DMS device.

Neutral gas is often referred to as a carrier gas, drift gas, buffer gas, etc. and these terms are considered interchangeable herein. The gas is at a pressure such that the mean free path of the ion, or ions, of interest is less than the dimensions of the drift tube. That is the gas pressure is chosen for viscous flow. Under conditions of viscous flow of a gas in a channel, conditions are such that the mean free path is very small compared with the transverse dimensions of the channel. At these pressures the flow characteristics are determined mainly by collisions between the gas molecules, i.e. the viscosity of the gas. The flow may be laminar or turbulent. It is preferred that the pressure in the drift tube is high enough that ions will travel a negligible distance, relative to the longitudinal length of the drift tube, therefore a steady-state ion mobility is achieved. An IMS can be used at different pressure conditions.

The apparatus and methods used for flow injection analysis typically include an injector valve, transfer lines, fluid line connections, an addition fluid delivery pump, a sprayer probe with internal volume for ESI and APCI sources and a switching valve when multiple injector valves are configured. Each of these elements adds to the dead volume or mixing volume encountered when delivering a sample solution into an API source in flow injection analysis. Added dead or mixing volumes can cause sample dilution due to diffusion or mixing of the sample with solvent during sample solution flow into an API source. Sample can adsorb to the walls of the valve, transfer line and probe transfer tube. Dilution of sample and loss of sample to the inner surfaces of the flow pathway results in reduced ion signal and analytical sensitivity. As liquid flow rates are reduced the sample solution spends more time in the transfer dead volumes. Increased transfer time results in increased sample dilution and loss to transfer surfaces. Adsorbed sample can bleed off valve, transfer line, connector and probe surfaces in subsequent injections, contributing chemical noise and interference peaks to acquired mass spectrum. Chemical noise or interference peaks due to contamination from prior injected sample can reduce the accuracy of quantitative measurements and compromise the limits of detection. Increased valve, connector, transfer line and probe surfaces require increased solvent flushing or cleaning time in between sample injections to minimize subsequent sample carry over or bleed. This required flushing increases solvent consumption and increases the time between injections. Increased cleaning time between injections decreases the number of samples that can be injected in a given time period, reducing sample throughput.

The invention allows rapid flow injection analysis over a wide range of liquid flow rates while minimizing solvent consumption and waste and eliminating all injector valves, fluid line connectors, transfer lines, probe liquid transfer tubes and additional liquid flow delivery system apparatus. Sample dilution or adsorption losses and solvent consumption are minimized with the invention and apparatus costs are reduced by elimination of components. Sample carry over or cross talk can be minimized with washing of reusable injection needles or eliminated with disposable or removable injection needles configured according to the invention. The invention comprises the configuration and use of an injector needle to draw up sample solution from a sample vial or container into the injector needle and attached solvent reservoir, transfer of the sample solution to an API source probe, passing of the injector needle through the API source probe channel and spraying of the sample solution from the tip of the injector needle into an API source. Ions are produced from the sprayed solution in the API source and are directed into the IMS where they are analyzed. API sources may include but are not limited to ESI, APCI or Inductively Coupled Plasma (OCP) ion sources.

Commercially available auto-injectors such as the Leap HTS PAL system are configured with syringes for the uptake, movement and injection of samples into injector valves. The syringes and attached injector needles are typically mounted to a programmable x-y-z position translator arm. Under pre-programmed control, sample solution is removed from a selected sample vial or vials, the loaded injector needle is moved to a position directly in-line with the bore of an ESI probe assembly and the injector needle is introduced through the bore of the ESI probe assembly in an ESI source. Some commercially available auto-injectors are configured with multiple syringes. FIA sample throughput can be increased according to the invention when such multiple syringe auto-injectors are used. Such a multiple syringe auto-injector configuration can be operated whereby one syringe is spraying sample solution into ES source while a second syringe is being flushed and cleaned prior to loading the next sample solution to be sprayed into the second injector needle and syringe. The syringes can be partially or completely filled with sample solution for each FIA run. The fill and spray liquid flow rates are determined by the syringe size used and the plunger movement rate as programmed in the auto-injector. Commercially available auto-injectors are configured to flush the internal bore of the syringe and injection needle and wash the injection needle external surface.

In one alternative embodiment, samples can be prepared using the same syringe and direct sprayed into the IMS device for analysis. The IMS device could be used to analyze complex samples using simple step sample preparation methods on the fly. These methods may include, but are not limited to, solid phase micro extraction (SPME) and micro extraction by packed sorbent (MEPS). A SPME fiber can be used to extract and preconcentrate gaseous or aqueous analytes; the analytes will then be desorbed into electrospray solvent for direct injection into the IMS for analysis. Alternatively, volatile and semi-volatile analytes could be thermally desorbed into the device and ionized in the desolvation region via SESI or other API methods. MEPS is a extraction technique that allows rapid sample preparation using in-syringe solid phase extraction. The syringe would then be directly inserted into the IMS for analysis. A variety of sorbents are commercially available.

For prior art IMS systems, the Faraday detectors are operated at ground or near-ground potential, and thus the other end of the drift tube, the ion source end, is set at high voltage. For positive ion detection, a positive voltage is applied at the ion source end; similarly for negative ion detection, a negative voltage is applied. State of art portable IMS systems have been generally developed for gas monitoring only, since the gas-phase sample can be guided into the ionization source via a non-conductive flow path. For an ESI source, the liquid sample needs to be delivered to the electrospray needle, and the liquid sample is generally conductive. This fact makes the handheld ESI-IMS challenging, since sample handling and injection pose a safety hazard. Developing a floating pre-amplifier that could be operated at high voltage allows the current invention to set the ionization source at ground and the Faraday detector at a high potential of the opposite polarity, i.e. positive potential for negative ions and negative potential for positive ions.

Figure 1:
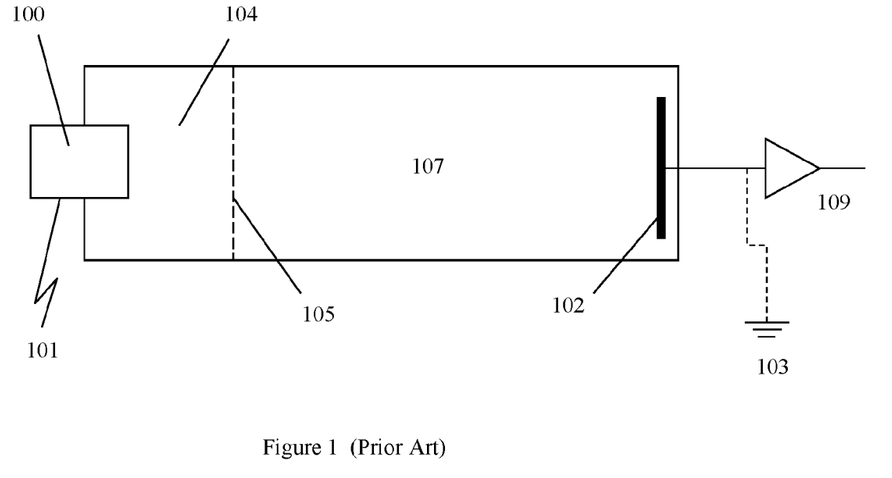
FIG. 1 shows schematic diagram of the prior state of the art IMS system.
Figure 2:
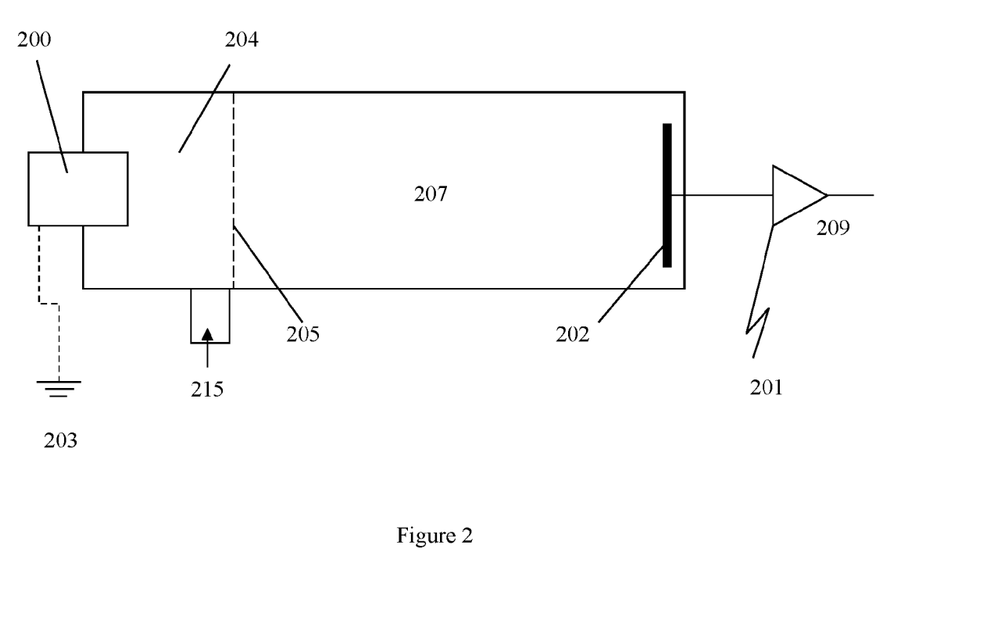
FIG. 2 shows schematic diagram of the IMS apparatus of this invention.

FIG. 1 shows the prior art IMS systems, the ionization source 100 is operated at the highest potential 101 of the drift tube and the Faraday ion detector 102 is operated at the lowest potential, substantially at ground potential 103. In various embodiments, a time of flight type of ion mobility spectrometer uses a ionization source 100, sample inlet, in case electrospray ionization source, the sample inlet is also the ionization source 100, desolvation/ionization (reaction) region 104, ion gate 105, drift region 107, aperture grid, ion detector 102, and pre-amplifier 109 that are organized on a continuous potential gradient connected with a resister chain. In case of prior art IMS, the ionization source or sample inlet are at high potential and ion detector is at low potential of this gradient. The current invention describes using an ion detector 202 (typically a Faraday plate) and a pre-amplifier 209 that operates at a high voltage 201, such as high voltage (potential) can either be positive or negative potential as shown in FIG. 2, in a range of 200-40000 V, in particular 1000V, 5000 V, 10,000 V with similar gain and rise time as the state-of-the-art amplifiers operating at near ground potential (such as the Keithley 428-PROG Programmable Current Amplifier, Cleveland, Ohio). In this non-limiting example, FIG. 2 shows a desolvation/ionization (reaction) region 204, ion gate 205, drift region 207, and a sample inlet port 215. This invention allows the ionization source 200, e.g. ESI or APCI source, and components that may need to be accessible during the analysis procedure to be set at substantially low voltage, such as, at ground potential 203. It will isolate users from high voltage components so that they can directly handle and inject samples into the IMS.

Basic operation of the IMS system will involve obtaining a sample and directly introducing the sample into the IMS device via direct syringe spray or other API source. The main advantages of the syringe direct spray include: 1) rapid testing, since a sample could be analyzed within one minute; 2) no cross contamination, since there is no carry-over from previous samples as the sample is directly delivered from the syringe to the desolvation region of the detector. Flow rates for common ESI methods are typically at about 1-10, 10-100, and can be substantially increase to 100-1000, 1000-5000 μL/min, etc., and each test may be completed in a time-span ranging from several milliseconds seconds a minute, depending on the amount of signal averaging required. This means that very little solvent is required. If the analyte is sufficiently concentrated such that direct measurement is possible, an aqueous sample may be directly diluted with organic solvents, such as methanol, for stable electrospray. The sample preparation method may involve: a 10 μL syringe may be preloaded with 1 μL methanol; subsequently 1 μL of aqueous sample would be drawn up, and the syringe would then be inserted into the ESI source for direct measurement. A thermal desorber/secondary electrospray ionization (SESI) source module could also be used, which would allow analysis of gas phase and solid phase samples. SESI involves spraying electrospray solvent to deliver charged solvent droplets into the desolvation region; the charged solvent droplets are then used to ionize gas-phase samples.

In one embodiment, the direct syringe spray method uses a single syringe that has a needle in the diameter that could be used to directly spray sample into the spectrometer. For this purpose, there is an electrical contact that is attached to the syringe needle, but no other assembly component is needed for this ionization source. The syringe is used to draw samples from a liquid reservoir (sampling) and then spraying the sample into the spectrometer using the same or a replacement needle. The single syringe needle spray ionization source can be used with an prior art ion mobility based spectrometer or the ion mobility based spectrometer that the ionization source is at ground or near ground potential.

The IMS system with the ionization source at near ground potential will not only benefit the direct analysis of liquid samples, but also allow easier sample introduction of gas and solid sample. With a thermal desorber, it can also be used to analyze gas phase and solid phase samples (first evaporated with the thermal desorber) and then ionize using SESI or other API methods. The combined thermal desorber/SESI subsystem will allow the user to switch between a direct liquid injection mode and a thermal desorption/gas sampling mode in-situ. The gas-phase sample, either directly from the surrounding environment or from thermal desorption of the solid-phase sample, is pulled into the desolvation region via the gas inlet and ionized by the charged droplets.

In various embodiments, the ground potential can also be located in the middle of a drift tube, such as the sample inlet before the ion gate. In this case, for positive ion measurement, the ionization source is positive potential, the sample inlet port location is at ground, and the Faraday detector is at negative potential; the potential gradient will be reversed for negative ion measurement. Setting the sample port at ground potential allow users directly insert sample into the sampling port without safety concerns.

Figure 3:
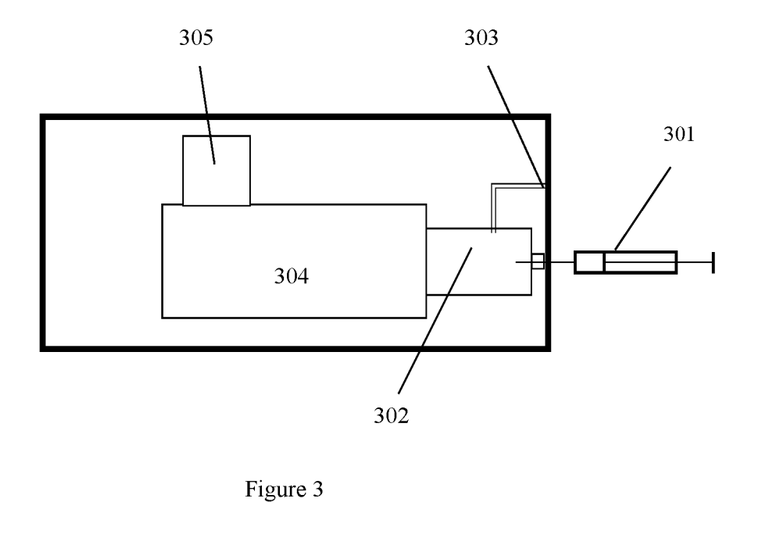
FIG. 3 shows the single syringe electrospray for IMS.

In one embodiment of direct syringe spray ion mobility spectrometer, as shown in FIG. 3 the liquid sample in syringe 301 is directly electrosprayed into the desolvation/reaction region 302 of the ion mobility spectrometer (where the curtain gas section is not shown). In addition, a gas sample inlet port 303 could be added to the desolvation region where the gas phase sample could be ionized undergoing secondary electrospray ionization. In case the syringe needle 301 is replace by other ionization sources operated at ground or near ground potential, the ionization process of the gas phase sample will undergo other secondary ionization processes. Ions formed in the desolvation region or reaction region are analyzed by ion mobility analyzer 304 in the drift gas that is preheated or mixed to designated temperature and/or other conditions using the gas preheating/mixer subsystem 305.

In one embodiment of the ESI-IMS system, the electrospray ionization source comprises an electrospray needle, curtain (cooling) gas section and desolvation region and other components of IMS. The ionization source is operated at substantially at atmosphere pressure. The curtain section is placed between desolvation region and electrospray needle (the ionization source), the curtain section is to substantially thermally isolate the electrosprayer needle from heated gas of desolvation region (desolvation gas).

The electrospray ionization source consists of an electrospray needle, curtain gas section and desolvation region. The ionize source is operated at substantially at atmosphere pressure. The lowered gas temperature at electrospray needle region will provide a favorable environment for electrospraying by avoiding boiling of the analyte solution in the electrospray needle and at the tip of electrospray needle, by high temperature gas. It is beneficial to have this curtain gas section to separate the electrospray needle from the high temperature desolvation, especially when a syringe needle is used as the electrospray needle without other additional components surround the bare needle tip. The electrospray needle is at a high electrical potential relative to the adjacent electrodes to generate charged droplets. The charged droplets generated from the electrospray needle will be transported to the desolvation region through the curtain gas section and desolvated at desolvation region and ions will be generated. The ions in the desolvation region will be gated to the drift region for ion mobility analysis. The ions in the desolvation region can be further transported to high vacuum to be analyzed by mass spectrometer. The curtain gas section provides positive or negative gas flow. For positive cooling gas flow, the cooling gas will be at lower temperature than the gas at the desolvation region, and will lower the gas temperature at the electrospray needle region. For negative cooling gas flow, the cooling gas flow will lower the gas temperature at the electrospray needle region than the gas temperature without negative cooling gas flow.

One embodiment of the invention is an ion mobility based spectrometer apparatus comprising: an ionization source that is connect to a first end drift tube and an detector that is connected to the second end of the drift tube; a high potential is applied to operate the spectrometer; at least one section of the ionization source is set at ground or substantially near ground potential; and at least one section of the detector and/or the preamplifier is set at the high potential by connecting to an high voltage power supply. The end of the ionization source is set at near ground potential that is a voltage that is substantial safe to touch. The high potential can be either positive or negative high potential. The ion mobility based spectrometer has a sample introduction port. The ground or near ground potential can be set at the sample introduction port. The sample introduction port may locate inside the ionization source or substantially downstream from the ionization source toward the ion detector.

Figure 4A:
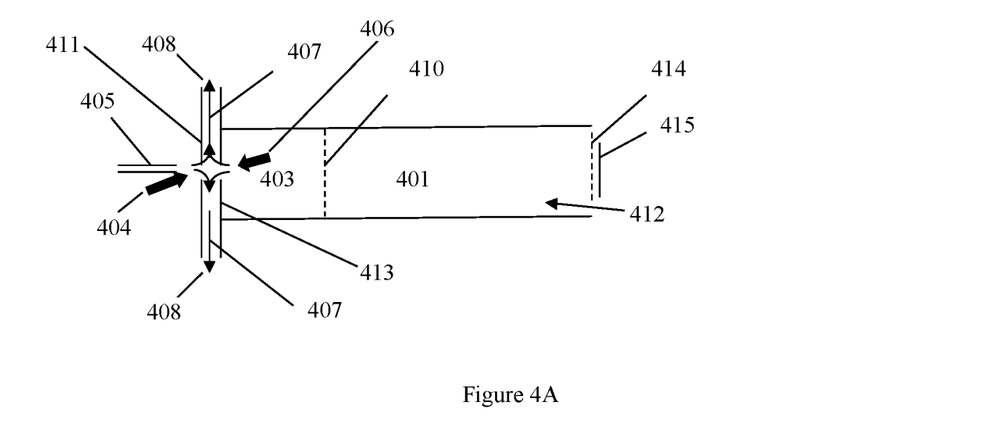
FIG. 4A-B shows an embodiment of the electrospray ionization source that could use a curtain gas section for heat isolation of high temperature drift gas from the electrospray needle.
Figure 4B:
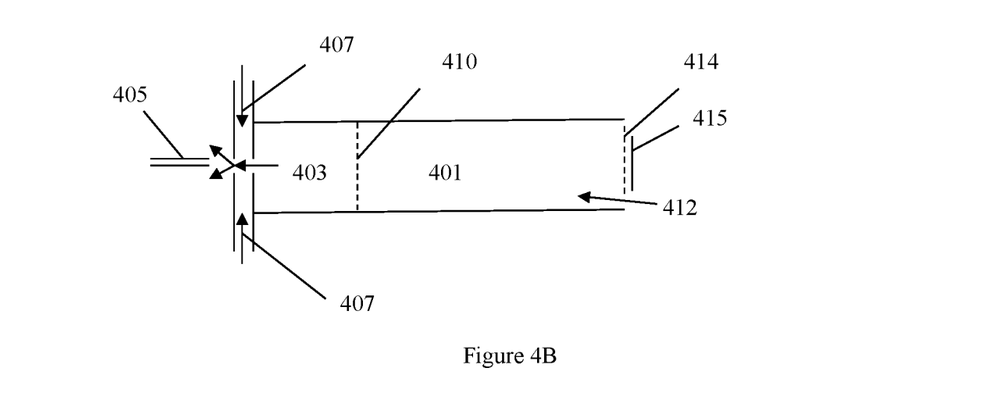

In various embodiments, an ion mobility based spectrometer (FIGS. 4A and 4B is shown as an example) does not necessary use an electrospray ionization source. FIGS. 4A and 4B shows a desolvation/ionization (reaction) region 403, ion gate 410, drift region 401, electrospray needle 405, drift gas flow 412, (optional) aperture grid 414 and a detector 415. FIG. 4A shows a non-limiting example of a curtain gas 407 at negative flow and FIG. 4B has a curtain gas 407 at positive flow. The curtain gas section could be used as a universal interface to bring charged particles or ions into the ion mobility based spectrometer. All ionization sources that are suitable the ion mobility based spectrometers could be used. Such sources could be, but not limited to, secondary electrospray ionization, DART ionization, DESI, MALDI, APCI, corona discharge, radioactive ionization.

One embodiment of the ion mobility based spectrometer apparatus has the ionization source set at a low potential for the spectrometer and the ion detector is set at a high potential whereby the ionization source on one end and the ion detector on the other end are in fluid communication. The low potential is the lowest potential for the spectrometer at ground or near ground potential whereby the high potential is the highest potential for the spectrometer. The high potential can be either positive or negative potential. The ion mobility based spectrometer can optionally have sample inlet which can be set at the lowest potential. The ionization source can be various, such as electrospray, DART, corona discharge, electron beam, radioactive $^{63}$Ni, but not limited to only these examples. When using electrospray ionization, a fixed needle can be used as well as a needle that is used for sampling and as the spray needle. Therefore, the ion mobility based spectrometer can be operated where an ionization source on one end is in fluid communication with an ion detector on the other end; setting the ionization source at a low potential of the spectrometer; and setting the ion detector at a high potential of the spectrometer. The low potential is set at the lowest potential for the spectrometer at ground or near ground potential. The high potential is set at the highest potential for the spectrometer and can be set at either positive or negative potential. The spectrometer can be operated using a sample inlet as well whereby the sample inlet is set at the lowest potential. The sample can be electrosprayed from a needle which can be used for sampling and spraying.

Another embodiment of the ion mobility based spectrometer apparatus has a curtain gas section which has at least two plates with an opening in the center (FIG. 4A). The plates are positioned to administrator gas flow as such: a low temperature cooling gas flow 404 enters the center hole of the first plate 411 on the needle side; a high temperature desolvation gas flow 406 enters the center hole of the second plate 413 on the desolvation section side; both gas flows are exhausted at a gas exit 408 located between the two plates. The plates can be set at different potentials that guide ions entering the first plate toward the second plate. The gas exit could be used as a gas inlet for the cooling gas flow and exhaust both cooling gas flow and the desolvation gas flow from the center hole of the first plate. Therefore, the ion mobility based spectrometer administers a curtain gas wherein the curtain gas flow is administered as such: a low temperature cooling gas flow enters a center hole of a first plate on the needle side; a high temperature desolvation gas flow enters the center hole of a second plate on the desolvation section side; both gas flows are exhausted at a gas exit. The plates can be set at different potentials that guide ions entering the first plate toward the second plate. The cooling gas flow can be used as a gas inlet and exhaust whereby both the cooling gas flow and the desolvation gas flow from the center hole of the first plate.

It is recognized that modifications and variations of the invention disclosed herein will occur to those of ordinary skill in the art and it is intended that all such modifications and variations be included within the scope of the appended claims. The contents of all of the patents and literature articles cited herein are incorporated into this specification by reference.

What is claimed is:

1. An ion mobility spectrometer apparatus comprising:
   a) an ionization source that produces charged particles or ions by electrospraying a solution in an electrospray needle when a voltage is applied to the electrospray needle, where, for each sample to be analyzed, the electrospray needle is placed in front of a negative flow curtain gas section;
   b) the negative flow curtain gas section bringing the charged particles or ions into a desolvation region is located between the electrospray needle and the desolvation region, wherein the negative flow curtain gas section has a first opening to the electrospray needle allowing charged particles or ions to enter, a second opening to the desolvation region, and a third opening where gas flows are exhausted;
   c) an ion gate that is located between the desolvation region and a drift region of the spectrometer; and
   d) a gas flow around the electrospray needle flows through the first opening into the negative flow curtain gas section; a high temperature desolvation gas flows from the desolvation region through the second opening into the negative flow curtain gas section; and both gas flows are exhausted through the third opening.

2. The ion mobility spectrometer apparatus of claim 1, wherein
   a) the ion detector is set at a high potential of the spectrometer by connecting to a high voltage power supply; and
   b) the electrospray needle is set at a low potential of the spectrometer.

3. The ion mobility spectrometer apparatus of claim 2, wherein the high potential is the highest potential for the spectrometer.

4. The ion mobility spectrometer apparatus of claim 2, wherein the high potential is either positive or negative potential.

5. The ion mobility spectrometer apparatus of claim 2, further comprises a sample inlet where a gas sample is introduced, and then ionized via a secondary electrospray ionization process.

6. The ion mobility spectrometer apparatus of claim 2, wherein the low potential is the lowest potential for the spectrometer at ground or near ground potential.

7. The ion mobility spectrometer apparatus of claim 1, wherein the needle or the needle attached to a syringe is used both for sampling and as the spray needle.

8. The ion mobility spectrometer apparatus of claim 1, where the curtain gas section further includes a first plate and a second plate, each of which has an opening in the center, and wherein the plates are set at different potentials that guide ions entering the first plate toward the second plate.

9. The ion mobility spectrometer apparatus of claim 1, wherein the third opening is used as a gas inlet at a different time period for a cooling gas flow, and both the cooling gas flow and the high temperature desolvation gas that flows from the desolvation region through the second opening into the curtain gas section are exhausted from the first opening to the electrospray needle.

10. A ion mobility spectrometer method comprises:
operating a ion mobility spectrometer with an electrospray needle, a negative flow curtain gas section, a desolvation region, an ion gate, and a drift region; wherein operating the ion mobility spectrometer includes putting an electrospray needle in front of the negative flow curtain gas section, applying a voltage to the electrospray needle, and electrospraying a solution in the electrospray needle; and administering gas flows as such: a gas flow around the electrospray needle flows through a first opening into the negative flow curtain gas section; a high temperature desolvation gas flows from the desolvation region through a second opening into the negative flow curtain gas section; and both gas flows are exhausted through a third opening in the negative flow curtain gas section.

11. The ion mobility spectrometer method of claim 10, further comprising setting the electrospray needle at a low potential of the spectrometer; and setting the ion detector at a high potential of the spectrometer by connecting to a high voltage power supply.

12. The ion mobility spectrometer method of claim 11, wherein the high potential is set at the highest potential for the spectrometer.

13. The ion mobility spectrometer method of claim 11, wherein the high potential is set at either positive or negative potential.

14. The ion mobility spectrometer method of claim 11, wherein the low potential is set at the lowest potential for the spectrometer at ground or near ground potential.

15. The ion mobility spectrometer method of claim 10, further comprise a sample inlet and ionizing the sample via a secondary electrospray ionization process.

16. The ion mobility spectrometer method of claim 10, further comprises using the needle or the needle attached to a syringe for sampling and spraying.

17. The ion mobility spectrometer method of claim 16, further comprise sample preparation methods in the syringe and/or needle including solid phase microextraction and microextraction by packed sorbent.

18. The ion mobility spectrometer method of claim 10, further comprise introducing a gas sample through a sample inlet and ionizing the sample by a secondary electrospray ionization process.

* * * * *